(12) United States Patent
Reinecke et al.

(10) Patent No.: US 7,074,201 B2
(45) Date of Patent: Jul. 11, 2006

(54) MEASUREMENT DEVICE FOR FITTING A BRACING DEVICE

(75) Inventors: Steven M. Reinecke, McKinney, TX (US); Thomas M. Grimm, Robbinsdale, MN (US); Timothy J. Walker, Farmington, MN (US)

(73) Assignee: AMEI Technologies, Inc., Wilmington, DE (US)

( * ) Notice: Subject to any disclaimer, the term of this patent is extended or adjusted under 35 U.S.C. 154(b) by 813 days.

(21) Appl. No.: 10/154,695

(22) Filed: May 23, 2002

(65) Prior Publication Data

US 2002/0193720 A1 Dec. 19, 2002

Related U.S. Application Data

(60) Provisional application No. 60/299,263, filed on Jun. 18, 2001.

(51) Int. Cl.
*A61F 5/00* (2006.01)
(52) U.S. Cl. .............................................. 602/5; 602/19
(58) Field of Classification Search .................... 602/5, 602/19; 128/870, 876; 2/338–340
See application file for complete search history.

(56) References Cited

U.S. PATENT DOCUMENTS

| 1,589,670 | A |   | 6/1926  | Vartia          |         |
|-----------|---|---|---------|-----------------|---------|
| 2,453,370 | A | * | 11/1948 | Hittenberger    | 602/19  |
| 2,835,247 | A |   | 5/1958  | Stabholc        | 128/78  |
| 3,029,810 | A |   | 4/1962  | Martin          | 128/78  |
| 3,351,053 | A |   | 11/1967 | Stuttle         | 128/78  |
| 3,420,230 | A |   | 1/1969  | Ballard         | 128/75  |
| 3,521,623 | A |   | 7/1970  | Nichols et al.  | 128/78  |
| 3,548,817 | A |   | 12/1970 | Mittasch        | 128/75  |
| 3,598,114 | A |   | 8/1971  | Lewis           | 128/78  |
| 3,889,664 | A |   | 6/1975  | Heuser et al.   | 128/75  |
| 3,926,182 | A |   | 12/1975 | Stabholz        | 128/75  |
| 4,135,503 | A |   | 1/1979  | Romano          | 128/78  |
| 4,269,179 | A |   | 5/1981  | Burton et al.   | 128/75  |
| 4,447,029 | A | * | 5/1984  | Chapman         | 248/246 |
| 4,497,517 | A |   | 2/1985  | Gmeiner et al.  | 297/231 |
| 4,552,135 | A |   | 11/1985 | Racz et al.     | 128/78  |

(Continued)

FOREIGN PATENT DOCUMENTS

DE 2637244 A1 6/1977

(Continued)

OTHER PUBLICATIONS

Reinecke, et al., "Traction Device," U.S. Appl. No.: 09/875,486, pending, Jun. 5, 2001.

(Continued)

*Primary Examiner*—Michael A. Brown
(74) *Attorney, Agent, or Firm*—Baker & McKenzie

(57) ABSTRACT

A measurement device includes a plurality of measurement belts and a plurality of side plates configured to be positioned around a user's body. A plurality of locking mechanisms each operable to adjustably couple one of the measurement belts and one of the side plates. The measurement device also includes a plurality of canting mechanisms coupling the measurement belts and the side plates. The canting mechanisms allow the associated measurement belt and side plate to rotate about associated pivots to allow the measurement belt and side plate to conform to user's body. The canting mechanisms also synchronize the movement of the side plate and the measurement belt such that movement of one causes an equivalent movement of the other. The point at which each measurement belt is coupled to the associated canting mechanism and the associated side plate is identifiable by one or more measurement indicators.

16 Claims, 5 Drawing Sheets

U.S. PATENT DOCUMENTS

| | | | |
|---|---|---|---|
| 4,559,933 A | 12/1985 | Batard et al. | 128/78 |
| 4,599,998 A | 7/1986 | Castillo | 128/77 |
| 4,622,957 A | 11/1986 | Curlee | 128/78 |
| 4,682,588 A | 7/1987 | Curlee | 128/78 |
| 4,685,668 A | 8/1987 | Newlin, Jr. | 272/123 |
| 4,691,696 A | 9/1987 | Farfan de los Godos | 128/78 |
| 4,702,235 A | 10/1987 | Hong | 128/78 |
| 4,715,362 A | 12/1987 | Scott | 128/75 |
| 4,721,102 A | 1/1988 | Pethybridge | 128/78 |
| 4,836,194 A | 6/1989 | Sebastian et al. | 128/78 |
| 4,884,562 A | 12/1989 | Stone | 128/78 |
| 4,898,185 A | 2/1990 | Fuller | 128/876 |
| 4,907,575 A | 3/1990 | Satterthwaite | 128/75 |
| 4,991,572 A | 2/1991 | Chases | 128/75 |
| 4,991,573 A | 2/1991 | Miller | 128/78 |
| 5,060,640 A | 10/1991 | Rasmusson | 128/80 |
| 5,062,414 A | 11/1991 | Grim | 128/68.1 |
| 5,111,807 A | 5/1992 | Spahn et al. | 606/244 |
| 5,144,943 A | 9/1992 | Luttrell et al. | 128/25 B |
| 5,188,586 A | 2/1993 | Castel et al. | 602/19 |
| 5,207,635 A | 5/1993 | Richards et al. | 602/19 |
| 5,256,135 A | 10/1993 | Avihod | 602/19 |
| 5,363,863 A * | 11/1994 | Lelli et al. | 128/876 |
| 5,382,226 A | 1/1995 | Graham | 602/32 |
| 5,403,266 A | 4/1995 | Bragg et al. | 602/5 |
| 5,437,617 A | 8/1995 | Heinz et al. | 602/19 |
| 5,441,479 A | 8/1995 | Chitwood | 602/18 |
| 5,462,518 A | 10/1995 | Hatley et al. | 602/36 |
| 5,586,969 A | 12/1996 | Yewer, Jr. | 602/19 |
| 5,651,764 A | 7/1997 | Chiu | 602/36 |
| 5,681,267 A | 10/1997 | Molino et al. | 602/19 |
| 5,690,609 A | 11/1997 | Heinze, III | 602/19 |
| 5,722,940 A | 3/1998 | Gaylord, Jr. et al. | 602/19 |
| 5,724,993 A | 3/1998 | Dunfee | 128/874 |
| 5,913,410 A | 6/1999 | Tsuchiya | 2/311 |
| 5,916,188 A | 6/1999 | Ousdal | 602/32 |
| 6,099,490 A | 8/2000 | Turtzo | 602/19 |
| 6,146,345 A | 11/2000 | Mignard | 602/19 |
| 6,401,350 B1 * | 6/2002 | Ford | 33/562 |
| 6,524,264 B1 * | 2/2003 | Hutchinson | 602/19 |

FOREIGN PATENT DOCUMENTS

| | | |
|---|---|---|
| DE | 19610018 A1 | 10/1996 |
| EP | 0864308 A1 | 9/1998 |
| WO | WO 02/069858 A1 | 9/2002 |

OTHER PUBLICATIONS

Reinecke, et al., "Lifting Mechanism for a Traction Device," U.S. Appl. No.: 09/875,332, pending, Jun. 5, 2001.

Reinecke, et al., "Canting Mechanism for an Ambulatory Support Device," U.S. Appl. No.: 09/875,473, pending, Jun. 5, 2001.

Reinecke, et al., "Traction Device Adjustment Mechanism and Method," U.S. Appl. No.: 09/875,315, pending, Jun. 5, 2001.

PCT, Notification of Transmittal of the International Search Report or the Declaration, 6 pages, Apr. 7, 2002.

PCT, Notification of Transmittal of the International Search Report or the Declaration, 7 pages, Apr. 7, 2002.

Unknown, "Office, Computer and Industrial Ergonomics," AliMed, Dedham, Massachusetts, 2 page brochure, 1993.

Unknown, "1992 Catalog," The Saunders Group, Inc., brochure, 2 pages, 1992.

Unknown, "Catalog for Rehabilitation Professionals," Flaghouse Rehab., 2 pages, Undated.

* cited by examiner

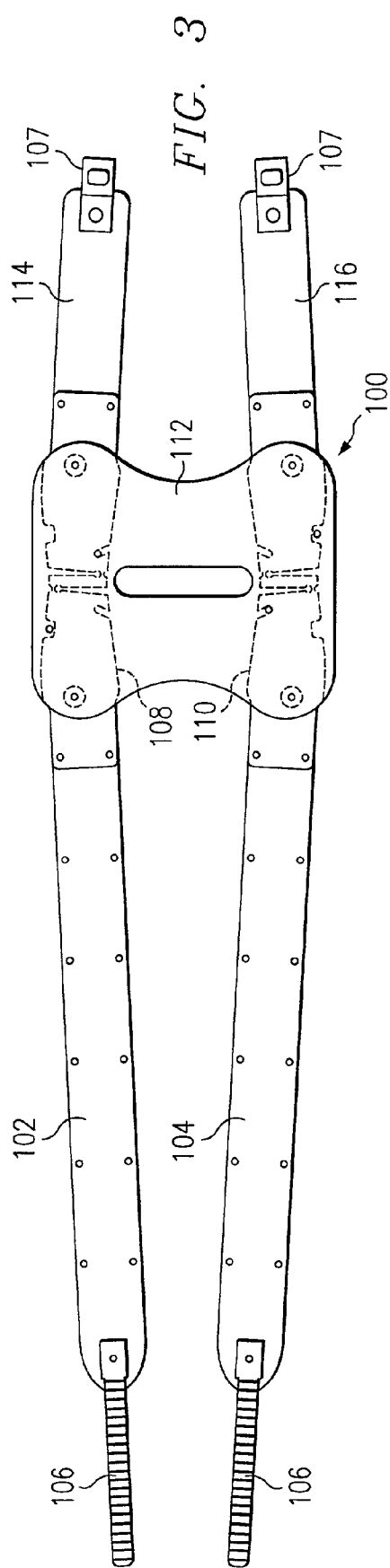
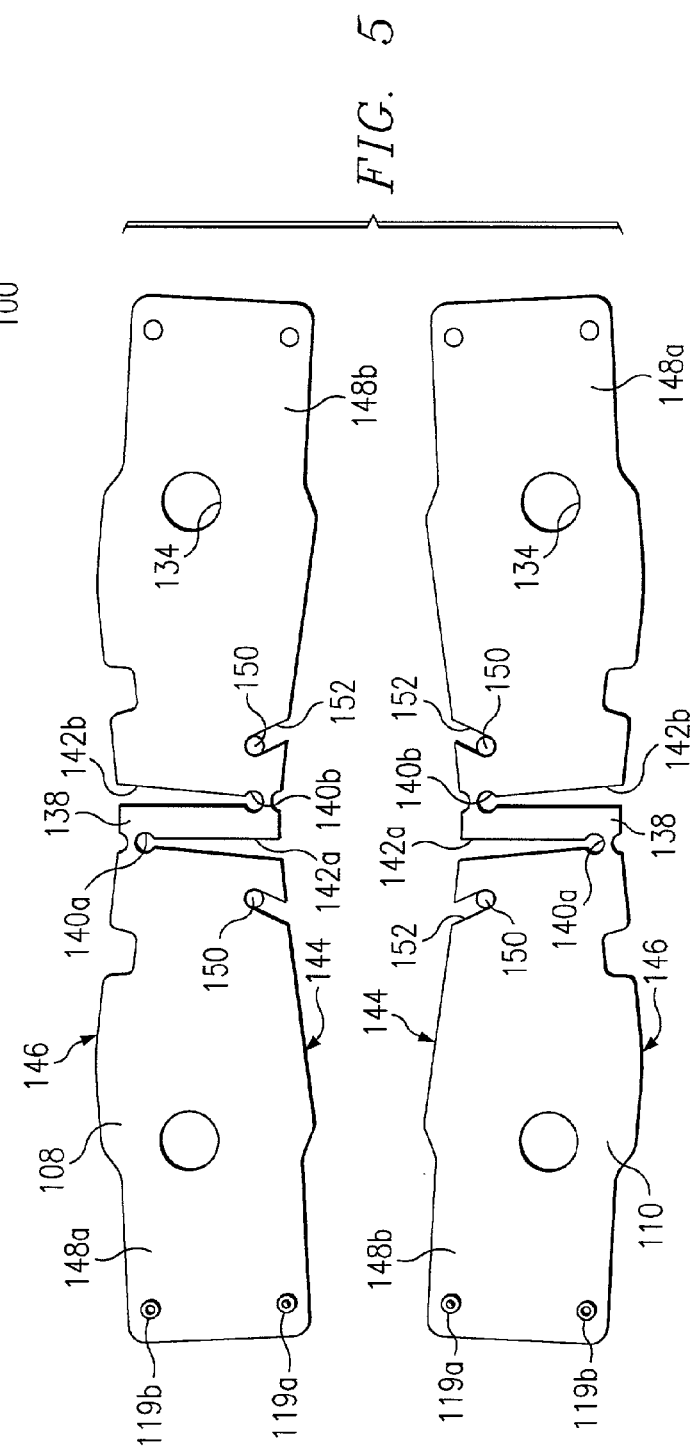

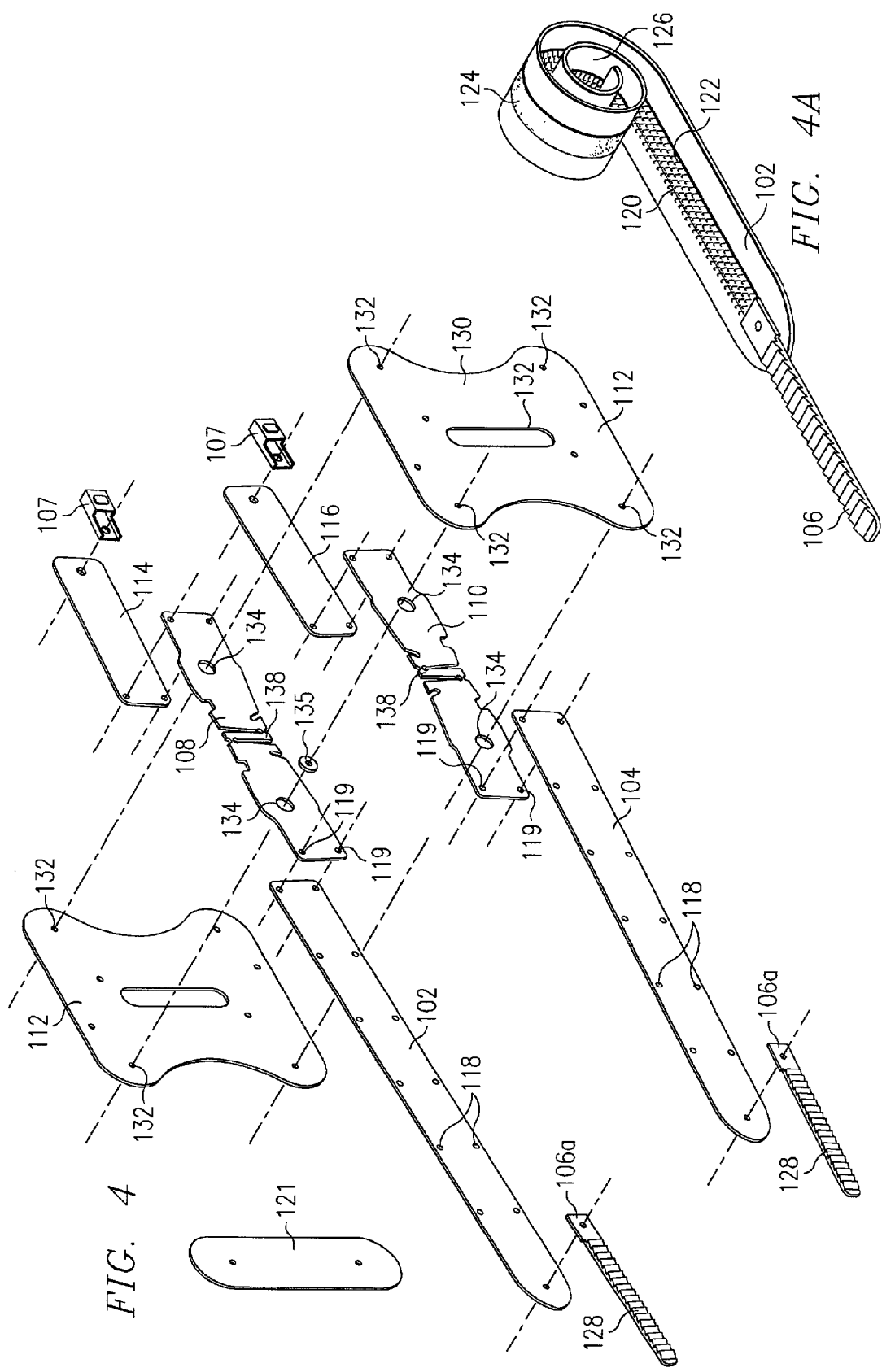

MEASUREMENT DEVICE FOR FITTING A BRACING DEVICE

RELATED APPLICATIONS

This application claims the benefit of U.S. provisional application Ser. No. 60/299,263, filed on Jun. 18, 2001, entitled "Measurement Device For Fitting Custom-Made Vest."

TECHNICAL FIELD OF THE INVENTION

This invention relates to the field of medical devices, and more particularly to a measurement device to be used in fitting a bracing device.

BACKGROUND OF THE INVENTION

Humans have long dealt with the pain, aggravation and loss of productivity arising from spinal injuries, particularly those to the low back. Most people at some point in their lives will be incapacitated by lower back pain which has become the second leading cause of pain next to headaches. The relative ease with which injuries to the spine and supporting musculature are incurred, as well as the debilitating effects of even slight injuries, merely adds to the overall severity of the problem of dealing with spinal injuries. The forms of treatment vary over the length of time that the patient experiences pain. Eighty percent of low back pain sufferers will heal over six weeks with minimal intervention. However, the remaining twenty percent of sufferers create the greatest challenges and cost to the medical system. After the acute phase, surgical intervention or more invasive forms of treatment may be selected. Minimal or non-invasive treatment methods are however preferred by patients before electing to surgical methods.

SUMMARY OF THE INVENTION

The present invention provides a measurement device for fitting a bracing device that substantially eliminates or reduces at least some of the disadvantages and problems associated with the previous measurement devices.

According to one embodiment of the present invention, a measurement device includes a plurality of measurement belts configured to be positioned around a user's body and a plurality of side plates configured to be positioned around a user's body. The measurement device also includes a plurality of locking mechanisms each operable to adjustably couple one of the measurement belts and one of the side plates. Additionally, the measurement device includes a plurality of canting mechanisms, and each couples one of the measurement belts and one of the side plates. The canting mechanisms allow the associated measurement belt and side plate to rotate about associated pivots to allow the measurement belt and side plate to conform to user's body. The canting mechanisms also synchronize the movement of the side plate and the measurement belt such that movement of one causes a substantially equivalent to movement of the other. The point at which each measurement belt is coupled to the associated canting mechanism and the point at which each measurement belt is coupled to the associated side plate is identifiable by one or more measurement indicators.

According to another embodiment of the invention, a method for measuring a user for a bracing device is provided that includes positioning a backplate of a fitting device on the back of a user. The backplate includes at least one canting mechanism. Each canting mechanism couples a measurement belt and an associated side plate and allows the measurement belt and the side plate to conform to the user's body. Each canting mechanism synchronizes the movement of the side plate and the measurement belt such that movement of one causes a substantially equivalent movement of the other. The method also includes coupling each measurement belt to the associated canting mechanism at a user-selectable point and positioning each measurement belt and the associated side plate about the body of the user. The method further includes coupling each measurement belt and the associated side plate using a locking mechanism. The method concludes by recording the point at which each measurement belt is coupled to the associated canting mechanism and the point at which each side plate is coupled to the associated measurement belt. Each of these points is identifiable by one or more measurement indicators.

Particular embodiments of the present invention provide on or more technical advantages. For example, certain embodiments provide a measurement device allowing a user to obtain multiple measurements to fit a bracing device to an individual user. In particular, the measurement device fits tightly around the body and simulates the feel and fit of the bracing device. The measurement device may also take into account bulky clothing that may be worn beneath the bracing device. Furthermore, particular embodiments of the present invention also include one or more canting mechanisms as part of the measurement device that allow opposing portions of the measurement device to rotate and conform to the contours of the user's body. Such canting mechanisms may also be included in the bracing device. Thus, the use of canting mechanisms in the measurement device mimics the fit of the bracing device. Other technical advantages may be readily apparent to those skilled in the art from the following figures, description and claims.

BRIEF DESCRIPTION OF THE DRAWINGS

For a more complete understanding of the present invention and for further features and advantages, reference is now made to the following description, taken in conjunction with the accompanying drawings, in which:

FIG. 3 illustrates an example measurement device;

FIG. 4 illustrates an exploded view of the measurement device of FIG. 3;

FIG. 5 illustrates example canting mechanisms of the measurement device of FIG. 3.

DETAILED DESCRIPTION OF THE DRAWINGS

Figure 1:
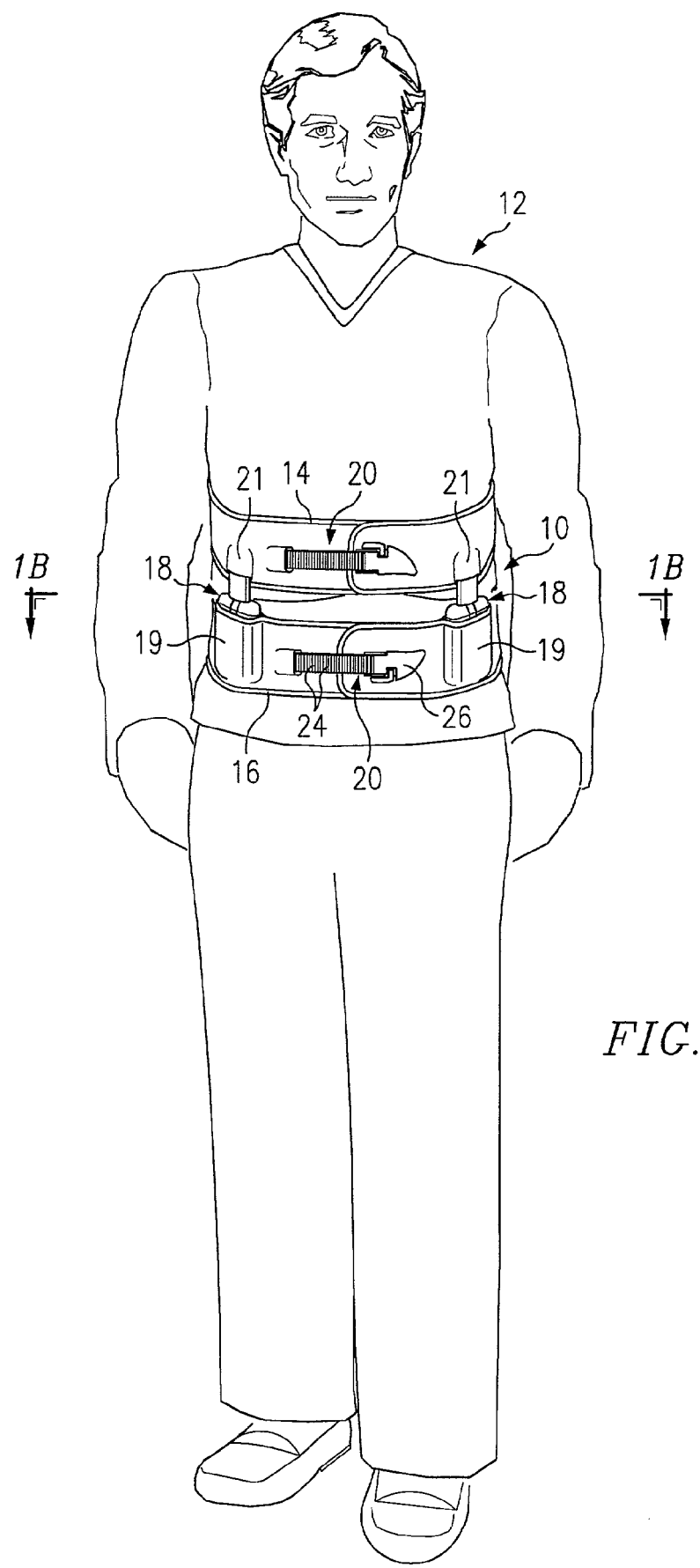
FIG. 1 illustrates an example spinal bracing device being worn by a user.

FIG. 1 illustrates an example spinal bracing device 10 being worn by a user 12. In this embodiment, bracing device 10 applies decompressive forces to the spine of user 12, which transfers body weight from the upper torso to the hips of user 12 and prevents compression and aggravation of lower back spinal conditions. In one embodiment, the off-loading forces are concentrated specifically on the lower spine, rather than across the entire spine. This effect is created by decompressive forces pushing upward and downward on the lower spine. In other embodiments, bracing device 10 may also be modified to create bracing in other portions of the body, such as the knee.

Spinal bracing device 10 includes an upper support belt 14 and a lower support belt 16; however in other embodiments, the decompression forces may be generated through various combinations of one or more belts. Support belts 14 and 16 may be formed in any suitable manner that allows positioning around the body of a user and transferring of a decompressive force to user 12. Example details of one embodiment of belts 14 and 16 are described in greater detail below in conjunction with FIG. 2.

Spinal bracing device 10 may include one or more lifting mechanisms 18. Although bracing device 10 is shown in FIG. 1 to include multiple lifting mechanisms 18, bracing device 10 may also be a static brace with any suitable static support mechanism. For example, lifting mechanism 18 might be replaced with static support members. Alternatively, bracing device 10 may include a traction brace with any suitable traction mechanism. The spinal bracing device 10 illustrated in FIG. 1 includes lifting mechanisms 18 to generate a decompressive, or tensile, force that may be transferred to the spine of user 12 through support belts 14 and 16. Lifting mechanisms 18 are coupled to a valve assembly to control pressurization of lifting mechanisms 18. Lifting mechanisms 18 are disposed within pouches 19 connected to lower support belt 16 and pouches 21 connected to upper support belt 14. When pressurized, lifting mechanisms 18 push upward on support belt 14 and downward on support belt 16, resulting in a decompressive force on the spine of user 12.

A proper fitting of spinal bracing device 10 about the body of user 12 is important. Fitting is accomplished, in part, through a pair of locking devices 20, one located on upper support belt 14 and one located on lower support belt 16 and through a common strap 22. Common strap 22 forms a part of both upper support belt 14 and lower support belt 16 and therefore allows uniform adjustment to both belts at the same time. Locking mechanisms 20 include a plurality of notches 24 and a latch 26 for locking mechanism 20 in place at a desired notch location. Locking mechanisms 20 may, however, be replaced with any suitable mechanism for locking belts 14 and 16 into a desired location, such as snaps, hook and loop type fasteners and other suitable fasteners Common strap 22 is described in greater detail below with reference to FIG. 2.

In operation, user 12 places spinal bracing device 10 around his lower torso and adjusts belts 14 and 16 using common strap 22 to a desired tension around his lower torso. Common strap 22 facilitates obtaining uniform tightness of both support belts 14 and 16. User 12 may then lock belts 14 and 16 in place using locking mechanisms 20. To apply bracing to the spine of user 12, a fluid is supplied to lifting mechanisms 18 to cause lifting mechanisms 18 to expand, thus pushing belt 14 upward and belt 16 downward. Because support belts 14 and 16 are tightly wrapped around the body of user 12, this decompressive force is transferred to the user's body and hence his spine. This relieves stress on the spine.

Bracing device 10 may be portable and wearable during everyday activities. Thus, device 10 may be applied at home, work, and play or during travel and at user's convenience. Therefore, a user is more likely to comply with therapy guidelines much more readily than if user 12 was required to travel to a clinic for therapy. The amount of force generated by the lifting mechanisms 18 may be controlled by the patient through a manual inflation device, valve assembly, or may alternatively be controlled with another suitable control device. In one embodiment, pressures generated within lifting mechanisms 18 offload approximately 50% of the body weight of user 12. A relief valve (not explicitly shown), may be provided to prevent overinflation. Such a relief valve may be situated such that user 12 may instantly relieve the pressure in lifting mechanisms 18 at any time. Spinal device 10 may also stabilize the torso, while still allowing flexibility. This stabilization prevents additional compressive forces in the spine due to bending and lifting.

Figure 2:
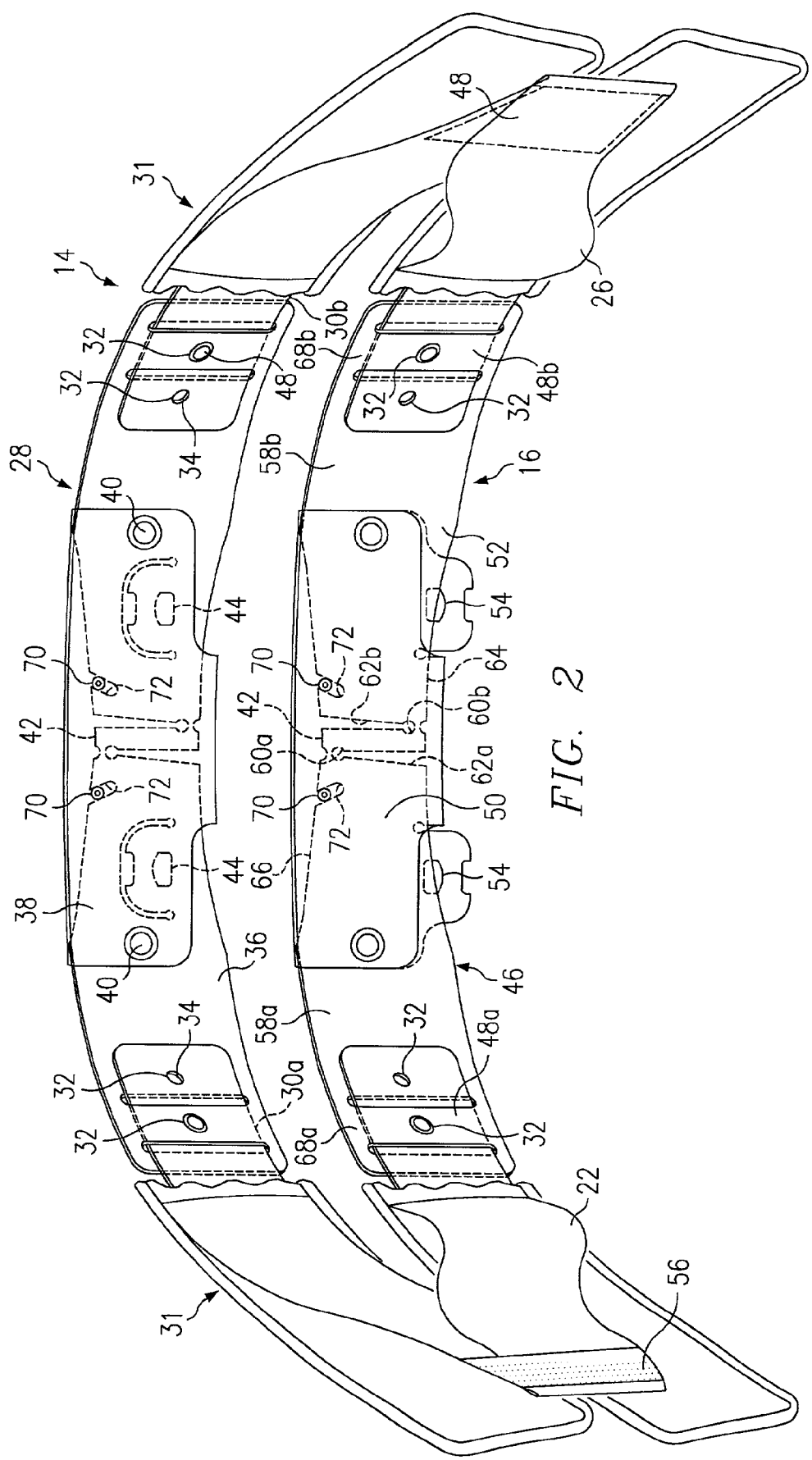
FIG. 2 illustrates portions of upper and lower support belts of the spinal bracing device of FIG. 1 in greater detail.

FIG. 2 illustrates portions of upper and lower support belts of the spinal bracing device of FIG. 1 in greater detail. Upper support belt 14 is formed from a back belt 28 and a pair of front belts 30. Some portions of front belts 30 are not illustrated in FIG. 2 for clarity of illustration. Front belts 30 are formed with a plurality of holes 32 allowing selective adjustment of the size of upper belt 14. In conjunction, back belt 28 includes a plurality of slits 35 for engaging front belts 30 and a holes 34 for meshing with holes 32 in front belts 30. Front belts 30 and back belt 28 may be locked together through a rivet or other connector placed through desired holes 32 and holes 34 on front belts 30 (not explicitly shown in FIG. 2). Surrounding front belts 30 and back belt 28 is an outer sleeve 31. Portions of outer sleeve 31 are cut away in FIG. 2. Outer sleeve 31 provides an attractive look to support belt 14 and also may provide cushioning comfort to user 12. Outer sleeve 31 may be formed from fabric or other suitable material and may be formed in a plurality of sections to facilitate selective access to back belt 28 and front belts 30 for adjustment.

Back belt 28 includes a strap 36 intermeshed between two plates 38. Back belt 28 may be coupled to front belts 30 of support belt 14 using holes 32 and 34 and an associated connector, with strap 36 being internal to plate 38 (closer to the user's body) to accommodate lifting mechanisms 18. In the example embodiment, strap 36 is coupled to plate 38 at two pivots 40. Pivots 40, along with a canting mechanism 42 incorporated in strap 36, allow strap 36 to move in relation to plate 38 (and thus in relation to lifting mechanisms 18) to assist in fitting support belts 14 and 16 to the user's body, as described below. Any appropriate component may be used to couple strap 36 and plate 38 at pivots 40 so as to allow strap 36 and plate 38 to rotate relative to one another at pivots 40. Additionally, it should be noted that support belt 14 may include a single belt that includes the features of both back belt 28 and front belts 30. Back belt 28 is a generally rigid member in the direction of generalized support (up or down in this example) and is disposed within outer sleeve 31 of belt 14. Front belts 30 are also generally rigid in the direction of support and may be formed from plastic or other suitable material.

The plate 38 that is positioned to the exterior of strap 36 is formed with notches 44 that are used to connect lifting mechanisms 18 to support belts 14 and 16. Notches 44 also couple to portions of lifting mechanisms 18 to facilitate transfer of a decompressive force from lifting mechanisms 18 to upper belt 14. Plate 38 is generally rigid in the direction of support such that it may transfer a force resulting from lifting mechanisms "pushing" it. Plate 38 may be formed from any suitable material that allows transferring of force from lifting mechanisms 18 to a belt 14; however in one embodiment, plate 38 is formed from plastic.

Lower support belt 16 is similar to upper support belt 14. Lower support belt 16 includes a back belt 46 and a pair of front belts 48. Back belt 46 and front belts 48 are substantially similar to upper back belt 28 and front belts 30 and include a plate 50 and a strap 52; however, plate 50 is formed with notches 54 facing downward rather than upward to allow transference of force from lifting mechanisms 18 in a downward direction. Also shown more clearly in FIG. 2 is common strap 26. Common strap 26 connects to both upper belt 14 and lower belt 16, allowing common adjustment of spinal bracing device 10 about the body of a user. In this example, hook and loop type fasteners 56, commonly known as Velcro™, are disposed on common strap 26 to secure strap 26 into place.

Strap 46 includes a first portion 58a and a second portion 58b that are coupled using canting mechanism 42. In one embodiment, canting mechanism 42 includes two hinges 60a and 60b. Plate 38 and canting mechanism 42 are typically positioned on the user's back near the spine when bracing device 10 is worn by the user. Portions 58 typically extend from the user's back and around the user's sides toward the user's front. When worn in such a manner, pivots 40 and hinges 60 of canting mechanism 42 allow portions 58 to conform to the contours of the user's body, and particularly to the areas of the thorax and the pelvis. Therefore, canting mechanism 42 may be used to more closely fit support belts 14 and 16 to users having a variety of different sizes and shapes, while maintaining substantial symmetry and more effective treatment.

Portions 58 and canting mechanism 42 may be integrally formed. For example, portions 58 and canting mechanism 42 may be formed from a single piece of plastic and hinges 60 may be formed by molding or cutting this piece of plastic into the desired shape. Alternatively, any other suitable method of fabricating these components from any appropriate material may be used. Hinges 60a and 60b may be formed by forming or cutting slots 62a and 62b, respectively, in strap 36. The term "slots" is meant to include both slits and wedges formed in strap 36. If slits are formed, the slits are pulled open to create wedges when strap 36 is coupled to plate 38. As illustrated in FIG. 2, slot 62a associated with hinge 60a begins at a first edge 64 of strap 36 and extends almost to a second edge 66 of strap 36. The remaining material of strap 36 between the end of slot 62a and second edge 66 of strap 36 forms hinge 60a. Furthermore, a circular or other cutout may be formed at the end of slot 62a near second edge 66 to aid in the opening of slot 62a and to reduce the resultant stresses on hinge 60a. Slot 62b is formed in a similar manner except that slot 62b begins at second edge 66 of strap 36 and extends almost to first edge 64 of strap 36. Hinge 60b is located proximate to first edge 64 and provides a different point of rotation than hinge 60a. Therefore, hinges 60a and 60b may be collectively referred to as a polycentric hinge.

If slots 62 are formed as wedges in strap 36, the width of wedges 62 and the angle at which wedges 62 are formed determines, at least in part, the range of movement of portions 58. For example, the greater the size of wedges 62, the more range of movement that will be allowed. If slots 62 are formed as slits, the slits are opened to form wedges having an appropriate size. Furthermore, the positioning of hinges 60 ensures that the movement of portions 58 is complementary. For example, if an end 68a of portion 58a moves up, then an end 68b of portion 58b will move up a substantially equal amount. This is because the upward movement of end 68a will cause slot 62a to close about hinge 60a, and this closure of hinge 62a will in turn cause slot 62b to open about hinge 60b (due to forces applied and the positioning of pivots 40). This closure of hinge 62b will in turn cause an upward movement of end 68b. Therefore, the design of canting mechanism 42 allows for the movement of portions 58a and 58b of strap 36 and synchronizes this movement.

Referring again to FIG. 2, depending upon which part of the user's body that back belt 28 is to be positioned around, one or more limitors 70 may be used to limit the movement of portions 58 in a certain direction. For example, if back belt 28 is to be positioned around the user's hips with first edge 64 of strap 36 nearest to the user's legs, then limitors 70 may be positioned as illustrated to allow portions 58 to move upward to accommodate the user's hips, but not allow downward movement of portions 58 past a certain point. Limitor slots 72 may be formed in strap 36 and may be configured and positioned such that when portions 58 are moved downward, limitor slots 72 engage with limitors 70 on plate 38 and prevent further downward movement of portions 58 with respect to plate 38. In this case, limitors 70 may be peg-like extensions from plate 38 on the side of plate 38 to which strap 36 is attached. Although limiting the downward movement of portions 58 is described, it should be understood that limitors 70 and limitor slots 72 may be positioned in other embodiments so as to limit the upward and/or downward movement of portions 58.

FIG. 3 illustrates an example measurement device 100. As previously stated, a proper fitting of spinal bracing device 10 about the body of user 12 is important. In this particular embodiment, fitting device 100 is configured to simulate the tightness of spinal bracing device 10 and allow gentle offloading forces to user 12 without slipping. Accordingly, when worn by user 12, fitting device 100 is similar in certain respects to spinal bracing device 10 as shown on user 12 in FIG. 1. Fitting device 100 provides accurate measurements to be used to customize spinal bracing device 10 to each user 12.

Upper measuring belt 102 is connected to an upper canting mechanism 108. The point of connection between upper measuring belt 102 and upper canting mechanism 108 provides a measurement reading, upper measuring belt measurement, to be used in customizing spinal bracing device 10 to user 12. Similarly, lower measuring belt 104 is connected to a lower canting mechanism 110 and provides another measurement reading, lower measuring belt measurement. Upper and lower measuring belts 102 and 104 are also connected to locking mechanisms 106. Fitting device 100 also includes an upper side plate 114 and a lower side plate 116. Upper side plate 114 and lower side plate 116 are connected to upper canting mechanism 108 and lower canting mechanism 110, respectively. In one embodiment, side plates 114 and 116 are connected to locking mechanisms 107. Upper side plate 114 and lower side plate 116 may be formed in any suitable manner that allows positioning around the body of a user 12. In one embodiment, the upper side plate 114 and lower side plate 116 are composed of a generally flexible, but non-elastic material. Example details of one embodiment of belts 102 and 104 are described in greater detail below in conjunction with FIG. 4.

Fitting device 100 also includes two backplates 112 that are coupled together to enclose canting mechanisms 108 and 110 between them. Canting mechanisms 108 and 110 may include portions that extend beyond the backplates 112 toward user's sides. Back plates 112 may be formed in any suitable manner that allows positioning around the body of a user 12. In one embodiment, backplates 112 are composed of a generally rigid material. Example details of one embodiment of canting mechanisms 108 and 110 and backplates 112 are described in greater detail in an exploded view of fitting device 100 in FIG. 5.

In operation, by placing fitting device 100 on the user's body and securing the locking mechanisms 106 to locking mechanisms 107, fitting device 100 provides user 12 with a plurality of measurement readings. Measuring belts 102 and 104 are snapped into place using fasteners 118 and 119. The point of connection of each belt 102 and 104 provides a measurement reading, as described above, to be used in customizing spinal bracing device 10 to user 12. Next, measuring belts 102 and 104 are wrapped around a first side of user 12 reaching the front of user 12. Similarly, side plates 114 and 116 are also wrapped around the other side of user 12 reaching the front of user 12. Locking mechanisms 107 each provide an additional measurement reading, upper side plate measurement and lower side plate measurement. The measurements may then be used to custom fit a spinal bracing device 10 to user 12. Padding or bulkiness of clothing material under the vest may be taken into account by inserting the measurements into a logarithmic or other appropriate equation. It should be noted, however that in other embodiments, the measurements may be generated through various combinations of one or more belts. The number of side plates included in fitting device 100 typically corresponds to the number of measuring belts, which should in turn correlate with the number of support belts on spinal bracing device 10. However, other appropriate arrangements may be used.

FIG. 4 illustrates an exploded view of the measurement device 100. Upper measuring belt 102 includes a plurality of fasteners 118 allowing selective attachment and adjustment of the size of upper measuring belt 102. Fasteners 118 may be evenly spaced along the length of upper measuring belt 102. A measurement indicator corresponds with the location of each fastener 118 along upper measuring belt 102. The measurement indicator provides upper measuring belt measurement to be used in customizing spinal bracing device 10 to user 12. In one particular embodiment, the measurement indicator corresponding with each fastener 118 is a letter. In conjunction with fasteners 118, upper canting mechanism 108 includes compatible fasteners 119 for connecting the upper measuring belt 102 to the upper canting mechanism 108. In one embodiment the fasteners are snaps with corresponding male and female parts. Fasteners 118 and 119 may, however, be replaced with any suitable fastener for coupling upper measuring belt 102 and upper canting mechanism 108. For example, the upper measuring belt 102 may include a cut-out corresponding to each fastener 118. When the upper measuring belt 102 is fastened to the upper canting mechanism 108, a letter may appear in the cut-out. Example details of one embodiment of fasteners 118 and 119 are described in greater detail below in conjunction with FIG. 5.

In one embodiment, hook and loop type fasteners 120, commonly known as Velcro™, are disposed along the length of upper measuring belt 102. Either the hook portion or the loop portion is attached along the length of the front side 122 of upper measuring belt 102 and the other of the hook portion or loop portion is attached along the length of the back side 124 of upper measuring belt 102. In operation, fasteners 118 and fasteners 119 are locked together such that upper measuring belt 102 will wrap snugly around the side of user 12 reaching the front of user 12. Excess length of upper measuring belt 102 may be rolled into a coil 126 to ensure that excess length will not impede a proper reading of measurement indicators corresponding with placement of fasteners 118a and 118b. Hook and Loop fasteners 122 and 124 then hold coil 126 in place.

Locking mechanism 106 is attached to the furthest end of upper measuring belt 102. The attachment of locking mechanism 106 may be made by rivets, adhesion, or any other appropriate manner of connection. As previously described, locking mechanism 106 of upper measuring belt 102 is configured to be coupled to locking mechanism 107 of upper side plate 114 to provide another measurement, upper side plate measurement, to be used in customizing spinal bracing device 10 to user 12. In the illustrated embodiment, locking mechanisms 106 are ratchet straps that include a plurality of notches 128, and locking mechanisms 107 are buckles compatible with the ratchet strap. Locking mechanisms 106 and 107 may, however, be replaced with any suitable mechanism for coupling upper measuring belt 102 and upper side plate 114 such that a snug fit is maintained, such as snaps, hook and loop type fasteners, or other suitable fasteners.

Upper side plate measurement may be provided by measurement indicators located on side plates 114 and 116 in the form of a ruler or any other measuring device. Upper side plate measurements may be provided by noting the measurement indicator corresponding to the location of the tip of the ratchet strap. Where, as described above, the measurement indicator corresponding with fasteners 118 may be a letter, the measurement indicator corresponding with locking mechanisms 106 and 107 may be a number or any other appropriate reference. Although measurement readings are described as including measurement indicators corresponding side plates 114 and 116, measurement indicators may be located elsewhere on fitting device 10. For example, measurement indicators could be located on the ratchet strap itself or any other appropriate location.

Lower measuring belt 104 is similar to upper measuring belt 102. Lower measuring belt 104 may include a plurality of snaps 118 or other fasteners compatible with fasteners 119 for connecting the lower measuring arm 104 with the lower canting mechanism 110. A measurement indicator corresponds with each location of a fastener 118a along lower measuring belt 104, providing another measurement reading, lower measuring belt measurement, to be used in customizing spinal bracing device 10 for user 12. In one embodiment, the measurement indicator may be a letter. For example, the lower measuring belt 104 may include a cut-out corresponding to each fastener 118. When the lower measuring belt 104 is fastened to the lower canting mechanism 110, a letter may appear in the cut-out. Additionally, hook and loop type fasteners 120 are also disposed along the length of lower measuring belt 104 for fixing excess length of lower measuring belt 102 when rolled into a coil 126. Locking mechanism 106 is attached to the farthest end of lower measuring belt 104 to couple lower measuring arm 104 to lower side plate 116 when fitting device 100 is worn by user 12. Coupling locking mechanism 106 on lower measuring belt 104 to locking mechanism 107 on the lower side plate 116 provides a another measurement, lower side plate measurement, to be used in customizing spinal bracing device 10 for user 12.

Fitting device 100 may also include a front plate 121 to ensure proper placement of the measuring belts on the body of user 12. Front plate 121 is configured to maintain fixed spacing between upper measurement belt 102 and lower measurement belt 104 at the point at which front plate 121 is coupled to measurement belts 102 and 104. Front plate 121 may be connected at its ends to the upper measuring belt 102 and the lower measuring belt 104 by utilizing fasteners 118 described above. In the alternative, a hook and loop fastener could be used on the back side of front plate 121 to be compatible with the hook and loop fastener that runs the length of the measuring belts, as described above. However, it is recognized that the connection may be made in any other suitable manner.

Fitting device 100 also includes two backplates 112. In the example embodiment, backplates 112 are substantially square in shape with indented side portions 130 and include an elliptical cutout in the center thereof. However backplates 112 may be any other appropriate shape. Backplates 112 are connected together to enclose canting mechanisms 108 and 110 between them. The connectors 132 between backplates 112 may be made by rivets, adhesion, or any other appropriate manner of connection. Connectors 132 may extend through pivot holes 134 and secure canting mechanisms 108 and 110 in place using pivots 135. Thus, in the example embodiment each canting mechanism 108 and 110 is held in place by two connectors 132. Pivots 135 assist in fitting measurement belts 102 and 104 and side plates 114 and 116 to the user's body by allowing canting mechanisms to rotate upward or downward about pivots 135. Pivots 135 may consist of a donut-shaped spacer which fits into pivot hole 135 of canting mechanisms 108 and 110. The outer rim of the spacer is fluted around the edge of the canting mechanism to secure the spacer in pivot hole 134. The hole in the center of the pivot 135 allows the rivet or other connector 132 to be placed through pivot 135. In operation, pivots 135, along with canting mechanism 136, allow measuring belts 102 and 104 and canting mechanisms 108 and 110 to rotate relative to one another at pivot 135.

FIG. 5 illustrates example canting mechanisms 108 and 110 of the measurement device 100. Canting mechanisms 108 and 110 include pivots 134, hinges 140, canting arms 148, and fasteners 119. The characteristics and operation of canting mechanism 138 are very similar to the canting mechanism described in FIG. 2 with regard to spinal bracing device 10. As was described with regard to FIG. 3, canting arms 148 are portions on opposing ends of canting mechanisms 108 and 110 that extend beyond backplates 112. Fasteners 119, for coupling the measuring belt to the canting mechanism, may be located on the canting arms 148.

As is illustrated in FIG. 5, hinges 140 and canting arms 148 may be integrally formed from a single piece of plastic. Hinges 140 may be formed by molding or cutting this piece of plastic into the desire shape. Alternatively, any other suitable method of fabricating these components from any appropriate material may be used. Hinges 140a and 140b may be formed by forming or cutting slots 142a and 142b, respectively, in canting mechanism 108. The term "slots" is meant to include both slits and wedges formed in canting mechanism 108. If slits are formed, the slits are pulled open to create wedges when canting mechanism 108 is coupled to backplates 112. As illustrated in FIG. 5, slot 142a associated with hinge 140a begins at a first edge 144 of canting mechanism 108 and extends almost to a second edge 146 of canting mechanism 108. The remaining material of canting mechanism 108 between the end of slot 142a and second edge 146 of canting mechanism 108 forms hinge 140a. Furthermore, a circular or other cutout may be formed at the end of slot 142a near second edge 146 to aid in the opening of slot 142a and to reduce the resultant stresses on hinge 140a. Slot 142b is formed in a similar manner except that slot 142b begins at second edge 146 of canting mechanism 108 and extends almost to first edge 144 of canting mechanism 108. Hinge 140b is located proximate to first edge 144 and provides a different point of rotation than hinge 140a. Therefore, hinges 140a and 140b may be collectively referred to as a polycentric hinge.

If slots 142 are formed as wedges in canting mechanism 108, the width of wedges 142 and the angle at which wedges 142 are formed determines, at least in part, the range of movement of canting mechanism 108. For example, the greater the size of wedges 142, the more range of movement that will be allowed. If slots 142 are formed as slits, the slits are opened to form wedges having an appropriate size. Furthermore, the positioning of hinges 140 ensures that the movement of canting mechanism 108 is complementary. For example, if a canting arm 148a of canting mechanism 108 moves up, then canting arm 148a of canting mechanism 108 will move up a substantially equal amount. This is because the upward movement of canting arm 148a will cause slot 142a to close about hinge 140a, and this closure of hinge 140a will in turn cause slot 142b to open about hinge 140b (due to forces applied and the positioning of pivots 134). The closure of hinge 140b will in turn cause an upward movement of canting arm 148a. Therefore, the design of hinges 140 allow for the movement of canting arms 148a and 148b of canting mechanism 108 and synchronizes this movement.

Canting mechanism 110 is a mirror image of canting mechanism 108. Thus the above description pertaining to the canting mechanism 108 applies equally to canting mechanism 110. However, because canting mechanism 110 is a mirror image of canting mechanism 108, second edge 146 of canting mechanism 108, located nearest the shoulders of user 12, corresponds with second edge 146 of canting mechanism 110, located nearest the spine of user 12.

Back plates 112 and canting mechanisms 108 and 110 are typically positioned on the user's back near the spine simulating the position of spinal bracing device 10 when worn by user 12, as shown in FIG. 1. When worn in such a manner, pivots 134 and hinges 140 of canting mechanism 108 allow canting arms 148 to conform to the contours of the user's body, and particularly to the areas of the thorax and the pelvis. Therefore, canting mechanism 108 mimics the movement of canting mechanism 42 of bracing device 10. Depending upon which part of the user's body that measuring belts 102 and 104 and side plates 114 and 116 are to be positioned around, one or more limitors 150 may be used to limit the movement of canting arms 148 of canting mechanism 110 in a certain direction. For example, if upper canting mechanism 108 is to be positioned near the user's upper or middle back, then limitors 150 may be positioned as illustrated to allow canting arms 148 to move upward to accommodate the shape of the user's upper torso, but to not allow upward movement of canting arms 148 past a certain point. Limitor slots 152 may be formed in canting mechanism 108 and may be configured and positioned such that when canting arms 148 are moved upward limitor slots 152 engage with limitors 150 on canting mechanism 108 and prevent further upward movement of canting arms 148 with respect to back plate 112. Although limiting the upward movement of canting mechanism 108 is described, it should be understood that limitors 150 and limitor slots 152 may be positioned in other embodiments so as to limit the upward and/or downward movement of canting mechanisms 108 and 110. For example, placement of limitors 150 in limitor slots 152 of canting mechanism 110 will allow downward movement of canting arms 148 to accommodate the shape of the user's hips rather than upper torso. Limitors 150 may be positioned to allow canting arms 148 to move downward movement, but to not allow downward movement of canting arms 148 past a certain point.

As described above in regard to FIG. 4, a plurality of fasteners 118 and 119 couple the canting arm 148 portions of canting mechanisms 108 and 110 to the measuring belts 102 and 104, respectively. FIG. 5 shows in greater detail a more particular embodiment, in which the fasteners are snaps with male parts 119a and female parts 119b. The embodiment further utilizes a reverse snap system to prevent user confusion in distinguishing the upper measuring belt 102 from the lower measuring belt 104 when attaching to canting arms 148a. As such, canting arms 148a have the male part 119a nearest first edge 144 and the female part 119b nearest second edge 146. In this manner, canting mechanisms 108 and 110 and the snaps 119 thereon are the mirror image of each other. The reverse snap system also requires that corresponding snaps 118 on the upper measuring belt 102 and snaps 118 on the lower measuring belt 104 are also reversed. By reversing the snaps, upper measuring belt 102 cannot be properly snapped to lower canting mechanism 110, and lower measuring belt 104 cannot be properly snapped to upper canting mechanism 108. For example, should lower measuring belt 104 be snapped to the non-corresponding upper canting mechanism 110, measuring belt 104 will be facing the wrong direction and locking mechanism 106 on measuring belt 104 will not couple to locking mechanism 106 on upper side plate 114. One technical advantage provided by the reverse snap system is that it ensures that fitting device 100 is properly placed on user 12 to render accurate measurements.

Figure 6:
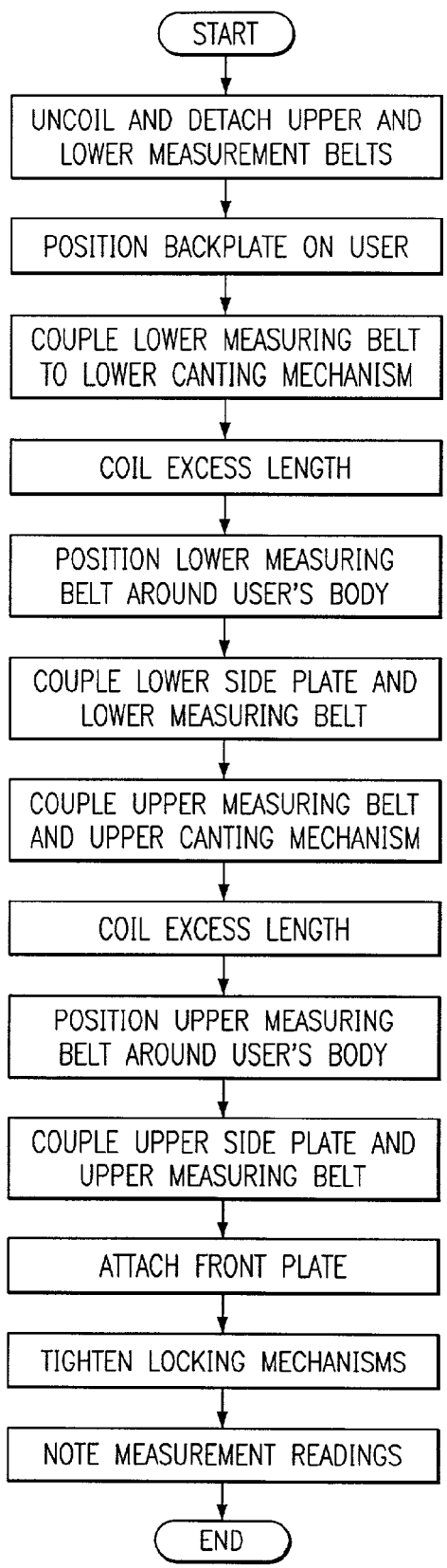
FIG. 6 illustrates an example method of using the measurement device of FIG. 3.

FIG. 6 illustrates an example method of using measurement device 100. Preferably, user 12 is assisted by a third party in the measuring process; however, user 12 may obtain measurement readings alone. At step 160, the measurer (user 12 or a third party) may begin by uncoiling measurement belts 102 and 104 to the fullest length and detaching measurement belts 102 and 104 from the canting mechanisms 108 and 110 (assuming measurement belts 102 and 104 are attached from a previous measurement). Backplate 112 is then positioned at step 162 on the user's back with the lower portion of the backplate located over the upper most point of the pelvis or "iliac crest." This is often the same location that the patient's pant's belt is worn. The iliac crest may also be felt on both sides of the hips. At step 164, the measurer couples lower measuring belt 104 to lower canting mechanism 110 using fasteners 119. Lower measuring belt 104 should be long enough to reach around user's body to user's front, but should be short enough to maintain a snug fit when locking mechanism 106 on lower measuring belt 104 and locking mechanism 107 on lower side plate are coupled. In one embodiment, lower measuring belt 104 may include a strip of hook and loop fasteners 124 or other appropriate fasteners running along the length of measurement belt 104. At step 165, any excess length of lower measuring belt 104 may be rolled into coil 126 using hook and loop fasteners 124, as was previously described with regard to FIG. 4. The point at which measurement belt 104 is coupled to lower canting mechanism 110 of connection provides a measurement reading, lower measuring belt measurement. Lower measuring belt measurement is provided by measurement indicators corresponding with each fastener 118 on lower measuring belt 104. As previously described with regard to FIG. 4, the measurement indicator corresponding with each fastener 118 may be a letter or a number. For example, the upper measuring belt 102 may include a cut-out corresponding to each fastener 118. When the upper measuring belt 102 is fastened to the upper canting mechanism 108, a letter may appear in the cut-out. This measurement may be noted at step 165 or later at step 182, as will be described below, for use in customizing spinal bracing device 10 to user 12.

At step 166, the lower side plate 116 and lower measuring belt 104 should each be wrapped around the user's body to the user's front. According to one embodiment, locking mechanism 106 of the lower measurement belt 104 is a ratchet strap and locking mechanism 107 of the lower side plate 116 is a buckle. In this embodiment, the ratchet strap may be secured through the buckle, to couple lower measuring belt 104 to lower side plate 116 at step 168. Ratchet strap and buckle may initially be loosely coupled about user 12 to secure fitting device 100 on user 12 and may be tightened at a later point, as is described below. Although a ratchet strap and buckle is described, any appropriate adjustable connector may be used.

Using fasteners 119, upper measuring belt 102 is coupled to upper canting mechanism 108 at step 170 in a similar manner as was described above with reference step 164. Upper measuring belt 102 should also be long enough to reach around user's body to user's front, but should be short enough to maintain a snug fit when locking mechanisms 106 and 107 are coupled. In one embodiment, upper measuring belt 102 may also include a strip of hook and loop fasteners 124 or other appropriate fasteners running along the length of measurement belt 102. At step 172, any excess length of upper measuring belt 102 may be rolled into coil 126 as was described above with reference to step 165. The point of connection of upper measuring belt 102 to upper canting mechanism 108 provides a measurement reading, upper measuring belt measurement. Upper measuring belt measurement is provided by measurement indicators corresponding with each fastener 118 on upper measuring belt 102. As previously described with regard to FIG. 4, the measurement indicator corresponding with each fastener 118 may be a letter or a number. For example, the lower measuring belt 104 may include a cut-out corresponding to each fastener 118. When the lower measuring belt 104 is fastened to the lower canting mechanism 110, a letter may appear in the cut-out. This measurement may be noted at step 172 or later at step 182, as will be described below, for use in customizing spinal bracing device 10 to user 12.

At step 174, upper measuring belt 102 and upper side plate 114 may then be wrapped around the user's body to the user's front. As described in regard to lower measuring belt 102 at step 168, the locking mechanism 106 of upper measuring belt 102 may include a ratchet strap and locking mechanism 107 of upper side plate 114 may include a buckle. At step 176, locking mechanisms 106 and 107 may be used by the measurer to couple upper measuring belt 102 to upper side plate 114. Ratchet strap and buckle may initially be loosely coupled about user 12 to secure fitting device 100 on user 12 and may be tightened at a later point, as is described below. While fitting device 10 is loosely coupled about user's body, front plate 121 may be attached, as step 178, to upper measuring belt 102 and lower measuring belt 104 to ensure proper placement of the measuring belts around the body. Step 178 may include the measurer using snaps 118 included on measurement belts 102 and 104 to couple opposing ends of front plate 121 to measurement belts 102 and 104 to ensure proper placement of measurement belts 102 and 104 about user's body. However, it is recognized that step 178 may be accomplished by fastening hook and loop fasteners 120 or in any other suitable manner.

At step 180, the measurer tightens locking mechanisms 106 and 107 of the upper and lower measurement belts. Step 180 may include adjusting locking mechanisms 106 and 107 such that fitting device 10 snugly fits user 12. Fitting device 10 should be tight enough to prevent movement of measurement belts 102 and 104 when grasped and pushed up and down. In this manner, fitting device 10 may simulate the tightness of bracing device 10 and allow gentle offloading of forces to the body without slipping. Once tightened, the measurer may obtain measurement readings at step 182. The point of connection of lower measuring belt 104 to lower side plate 116 provides a measurement reading, lower side plate measurement. Similarly, the point of connection of upper measuring belt 102 to upper side plate 114 provides a measurement reading, upper side plate measurement. Measurement indicators may be located on side plates 114 and 116 in the form of a ruler or other measuring device. Upper and lower side plate measurements may be provided by noting the measurement indicator corresponding to the location of the tip of the ratchet strap. As previously described with regard to FIG. 4, the measurement indicator corresponding with each side plate may be a number or a letter. Where the measurer has failed to note the upper lower measuring belt measurement and upper measuring belt measurement as described above, step 182 also includes taking note of these measurements.

The measurement readings obtained by properly placing fitting device 10 on user 12 may be used to customize spinal bracing device 10 to each user 12. As described above, the measurement readings may include the upper measuring belt measurement, the lower measuring belt measurement, the upper side plate measurement, and the lower side plate measurement. Although measurement readings are described above as including measurement indicators corresponding to fasteners 118 and side plates 114 and 116, measurement indicators may be located elsewhere on fitting device 10. For example, measurement indicators could be located on the ratchet strap itself or any other appropriate location. Additionally, padding or bulkiness of clothing material under the vest may be taken into account by inserting the measurements into a logarithmic or other appropriate equation.

Although the illustrated embodiment and the example method include the use of two measurement belts and two side plates, it should be noted that other embodiments may include combinations of one or more belts. The number of side plates included in fitting device 100 typically corresponds to the number of measuring belts, which should in turn correlate with the number of support belts of spinal bracing device 10. However other appropriate arrangements may be used. Additionally, the measurer may proceed through the method of using the measurement device as shown in steps 160–182 in FIG. 6 and as described above. However, it is recognized that one skilled in the art may perform the steps of the method in any suitable order.

Although the present invention has been described with several embodiments, numerous changes, substitutions, variations, alterations, transformations, and modifications may be suggested to one skilled in the art, and it is intended that the present invention encompass all such changes, substitutions, variations, alterations, transformations, and modifications as fall within the spirit and scope of the appended claims.

What is claimed is:

1. A measurement device for fitting a bracing device, comprising:
    a plurality of measurement belts configured to be positioned around a user's body;
    a plurality of side plates configured to be positioned around a user's body;
    a plurality of locking mechanisms each operable to adjustably couple one of the measurement belts and one of the side plates; and
    a plurality of canting mechanisms each coupling one of the measurement belts and one of the side plates, each canting mechanism operable to:
        allow the associated measurement belt and side plate to rotate about associated pivots to allow the measurement belt and side plate to conform to user's body; and
        synchronize the movement of the side plate and the measurement belt such that movement of one causes a substantially equivalent movement of the other;
    the point at which each measurement belt is coupled to the associated canting mechanism and the point at which each measurement belt is coupled to the associated side plate being identifiable by one or more measurement indicators.

2. The device of claim 1, wherein each locking mechanism comprises a ratchet strap and a buckle, the ratchet strap coupled to the measurement belt and configured to adjustably couple to the buckle, which is coupled to the associated side plate.

3. The device of claim 1, wherein the canting mechanisms are pivotally coupled to at least one backplate.

4. The device of claim 3, wherein the canting mechanisms are pivotally coupled between two backplates.

5. The device of claim 1, farther comprising a front plate adjustably coupled to at least two measurement belts, the front plate configured to maintain fixed spacing between the measurement belt at the points ax which the front plate is coupled to the measurement belts.

6. The device of claim 1, wherein the measurement belt comprises a plurality of snaps operable to couple the measurement belt to the canting mechanism, the snaps configured to restrict coupling of the canting mechanism to only one of the plurality of measurement belts.

7. The device of claim 1, wherein the measurement belt comprises a hook and loop fastener configured to allow excess length of measurement belt to be coiled at the point at which the measurement belt is coupled to the canting mechanism.

8. The device of claim 1, wherein the canting mechanism comprises a plurality of hinges, each hinge formed integrally from a single piece of material.

9. The device of claim 8, wherein the hinges collectively form a polycentric hinge.

10. The device of claim 8, wherein each hinge is formed by cutting a slot in the canting mechanism, a first slot being cut from a first edge of the canting mechanism apposite a first hinge and a second slot being cut from a second edge of the canting mechanism opposite a second hinge.

11. The device of claim 1, wherein the canting mechanism comprises one or more limitors that each limit the movement of a portion of the canting mechanism when a limitor notch formed in the portion engages with the limitor.

12. A method for measuring a user for a bracing device comprising:
    positioning a backplate of a fitting device on the back of a user, the backplate including at least one canting mechanism, each canting mechanism operable to:
        couple a measurement belt and an associated side pirate;
        allow the associated measurement belt and the associated side plate to rotate about associated pivots to allow the measurement belt and the side plate to conform to user's body; and
        synchronize the movement of the side plate and the measurement belt such that movement of one causes a substantially equivalent movement of the other;

coupling each measurement belt to the associated canting mechanism at a user-selectable point;

positioning each measurement belt and the associated side plate about the body of the user;

coupling each measurement belt and the associated side plate using a locking mechanism; and recording the point at which each measurement belt is coupled to the associated canting mechanism and the point at which each side plate is coupled to the associated measurement belt, each of these points being identifiable by one or more measurement indicators.

13. The method of claim 12, further comprising coupling a front plate between a plurality of measurement belts to maintain a fixed spacing between the measurement belts at the points at which the front plate is coupled to the measurement belts.

14. The method of claim 12, wherein:

the locking mechanism comprises a ratchet strap and a buckle, the ratchet strap coupled to the measurement belt and configured to adjustably couple to the buckle, which is coupled to the associated side plate; and coupling each measurement belt and the associated side plate using a locking mechanism comprises inserting the ratchet strap into the buckle until the measurement belts conform around the user's body.

15. The method of claim 12, further comprising coupling the measurement belt to the canting mechanism using a plurality of snaps on each of the measurement belt and the canting mechanism, the snaps configured to restrict coupling of the canting mechanism to only one of the plurality of measurement belts.

16. The method of claim 12, further comprising coiling an excess length of the measurement belt at the point at which the measurement belt is coupled to the canting mechanism.

* * * * *

UNITED STATES PATENT AND TRADEMARK OFFICE
CERTIFICATE OF CORRECTION

| | | |
|---|---|---|
| PATENT NO. | : 7,074,201 B2 | Page 1 of 1 |
| APPLICATION NO. | : 10/154695 | |
| DATED | : July 11, 2006 | |
| INVENTOR(S) | : Reinecke et al. | |

It is certified that error appears in the above-identified patent and that said Letters Patent is hereby corrected as shown below:

Column 14, Line 28, delete the word "ax" and insert in lieu thereof the word -- at --

Column 14, Line 47, delete the word "apposite" and insert in lieu thereof the word -- opposite --

Column 14, Line 60, delete the word "pirate" and insert in lieu thereof the word -- plate --

Signed and Sealed this

Twentieth Day of February, 2007

JON W. DUDAS
*Director of the United States Patent and Trademark Office*